US009289469B2

(12) United States Patent
Wilcox et al.

(10) Patent No.: US 9,289,469 B2
(45) Date of Patent: Mar. 22, 2016

(54) DEPLETING IMMUNOSUPPRESSIVE MONOCYTES WITHIN A MAMMAL

(75) Inventors: Ryan A. Wilcox, Rochester, MN (US); Thomas E. Witzig, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 211 days.

(21) Appl. No.: 13/394,787

(22) PCT Filed: Sep. 7, 2010

(86) PCT No.: PCT/US2010/048002
§ 371 (c)(1),
(2), (4) Date: Mar. 7, 2012

(87) PCT Pub. No.: WO2011/031676
PCT Pub. Date: Mar. 17, 2011

(65) Prior Publication Data
US 2012/0171207 A1  Jul. 5, 2012

Related U.S. Application Data

(60) Provisional application No. 61/241,227, filed on Sep. 10, 2009.

(51) Int. Cl.
A61K 39/00 (2006.01)
A61K 38/17 (2006.01)
(52) U.S. Cl.
CPC .................................. *A61K 38/1774* (2013.01)
(58) Field of Classification Search
None
See application file for complete search history.

(56) References Cited

U.S. PATENT DOCUMENTS

| 6,162,432 | A | 12/2000 | Wallner et al. | |
|---|---|---|---|---|
| 6,376,202 | B1 | 4/2002 | Davis | |
| 2004/0265315 | A1* | 12/2004 | Dingivan et al. | 424/155.1 |
| 2006/0111272 | A1* | 5/2006 | Roberts et al. | 514/2 |
| 2006/0148008 | A1 | 7/2006 | Hart | |
| 2007/0031443 | A1 | 2/2007 | Vaishnaw et al. | |

FOREIGN PATENT DOCUMENTS

WO  WO 03/009740  2/2003

OTHER PUBLICATIONS

Wilcox et al. (Blood, (Nov. 2009) vol. 114, No. 22. Abstract No. 464).*
Clinical trial NCT00438802 published on clinicaltrials.gov and updated on Jul. 23, 2008, pp. 1-4.*
Lin et al. (Blood, (Nov. 16, 2008) vol. 112, No. 11, pp. 300).*
Historical perspective on the development of ClinicalTrials.gov (updated Jan. 7, 2010, pp. 1-3).*
Strom et al. (Therapeutic Immunology edited by Austen et al., Blackwell Science, Cambridge, MA, 1996; pp. 451-456).*
Haider et al., The Journal of Immunology, 2007, 178: 7442-7449.*
Strauss-Ayali et al., J. Leukoc. Biol. 82: 244-252; 2007.*
Hoffman et al., Clin. Exp. Immunol. 1997; 110:63-71.*
Altomonte et al., Cancer Research 53, 3343-3348. Jul. 15, 1993.*
Gabrilovich et al., Nature Reviews Immunology, Mar. 2009, pp. 162-174.*
Hoechst et al. (Gastroenterology, 2008;135:234-243).*
Asadullah et al., "Immunodepression following neurosurgical procedures," *Critical Care Medicine*: 23(12):1976-1983, Dec. 1995.
Asadullah et al., "Very low monocytic HLA-DR expression indicates high risk of infection—immunomonitoring for patients after neurosurgery and patients during high dose steroid therapy," *Eur J Emerg Med.*, 2(4):184-190, Dec. 1995.
Axtelle and Pribble, "IC14, a CD14 specific monoclonal antibody, is a potential treatment for patients with severe sepsis," *J Endotoxin Res.*, 7(4):310-314, 2001.
Chamian et al., "Alefacept (anti-CD2) causes a selective reduction in circulating effector memory T cells (Tem) and relative preservation of central memory T cells (Tcm) in psoriasis," *J Transl Med.*, 5:27, Jun. 2007.
Crawford et al., "CD2 engagement induces dendritic cell activation: implications for immune surveillance and T-cell activation," *Blood*, 102(5):1745-1752, print Sep. 2003, Epub Apr. 2003.
Diaz-Montero et al., "Increased circulating myeloid-derived suppressor cells correlate with clinical cancer stage, metastatic tumor burden, and doxorubicin-cyclophosphamide chemotherapy," *Cancer Immunol Immunother.*, 58(1):49-59, print Jan. 2009, Epub Apr. 2008.
Filipazzi et al., "Identification of a new subset of myeloid suppressor cells in peripheral blood of melanoma patients with modulation by a granulocyte-macrophage colony-stimulation factor-based antitumor vaccine," *J Clin Oncol.*, 25(18):2546-2553, Jun. 2007.
Gabrilovich and Nagaraj, "Myeloid-derived suppressor cells as regulators of the immune system," *Nat Rev Immunol.*, 9(3):162-174, Mar. 2009.
GenBank® gi No. 156071471 (accession No. NM_001767), Sep. 2008, 3 pages.
GenBank® gi No. 156071472 (accession No. NP_001758), Sep. 2008, 2 pages.
GenBank® gi No. 221316611 (accession No. NM_001779), Feb. 2008, 3 pages.
GenBank® gi No. 4502677 (accession No. NP_001770), Feb. 2008, 2 pages.
Hoechst et al., "A new population of myeloid-derived suppressor cells in hepatocellular carcinoma patients induces CD4(+)CD25(+)Foxp3(+) T cells," *Gastroenterology*, 135(1):234-243, print Jul. 2008, Epub Mar. 2008.

*Primary Examiner* — Zachary Skelding
(74) *Attorney, Agent, or Firm* — Fish & Richardson P.C.

(57) ABSTRACT

This document provides methods and materials involved in depleting immunosuppressive monocytes (e.g., $CD14^+/DR^-$ or $CD14^+/DR^{low}$ monocytes) within a mammal. For example, methods and materials involved in using a CD2 binding molecule (e.g., alefacept) to deplete immunosuppressive monocytes within a mammal (e.g., a human) are provided.

13 Claims, 2 Drawing Sheets

(56) References Cited

OTHER PUBLICATIONS

Hoffmann et al., "Anti-CD2 (OX34) MoAb treatment of adjuvant arthritic rats: attenuation of established arthritis, selective depletion of CD4+ T cells, and CD2 down-modulation," *Clin Exp Immunol.*, 110(1):63-71, Oct. 1997.

Höflich et al., "Regulatory immunodeficiency and monocyte deactivation Assessment based on HLA-DR expression," Clinical and Applied Immunology Reviews 2(6):337-344, Oct.-Dec. 2002.

Iwakami et al., "Granulocyte and monocyte adsorption apheresis therapy modulates monocyte-derived dendritic cell function in patients with ulcerative colitis," *Ther Apher Dial.*, 13(2):138-146, Apr. 2009.

Miller et al., "Specific interaction of lymphocyte function-associated antigen 3 with CD2 can inhibit T cell responses," J. Exp. Med., 178(1):211-222, Jul. 1993.

Morimura et al., "Monocyte subpopulations in human gliomas: expression of Fc and complement receptors and correlation with tumor proliferation," *Acta Neuropathol.*, 80(3):287-294, 1990.

Ostrand-Rosenberg and Sinha, "Myeloid-derived suppressor cells: linking inflammation and cancer," *J Immunol.*, 15;182(8):4499-4506, Apr. 2009.

Peters et al., "Acquired immunoparalysis in paediatric intensive care: prospective observational study," *BMJ*, 319:609, Sep. 1999.

Rapp et al., "Cellular immunity of patients with malignant glioma: prerequisites for dendritic cell vaccination immunotherapy," *J Neurosurg*, 105(1):41-50, Jul. 2006.

Schimke et al., "Anti-CD14 mAb treatment provides therapeutic benefit after in vivo exposure to endotoxin," Proc Natl Acad Sci U S A., 95(23):13875-13880, Nov. 1998.

Serafini et al., "Myeloid-derived suppressor cells promote cross-tolerance in B-cell lymphoma by expanding regulatory T cells," *Cancer Res.*, 68(13):5439-5449, Jul. 2008.

Serafini et al., "Phosphodiesterase-5 inhibition augments endogenous antitumor immunity by reducing myeloid-derived suppressor cell function," *J Exp Med.*, 203(12):2691-2702, Nov. 2006.

Sester et al., "Strong depletion of CD14(+)CD16(+) monocytes during haemodialysis treatment," *Nephrol Dial Transplant.*, 16(7):1402-1408, Jul. 2001.

Sido et al., "Modulation of the CD2 receptor and not disruption of the CD2/CD48 interaction is the principal action of CD2-mediated immunosuppression in the rat," *Cell Immunol.*, 182(1):57-67, Nov. 1997.

Sinha et al., "Proinflammatory S100 proteins regulate the accumulation of myeloid-derived suppressor cells," *J Immunol.*, 181(7):4666-4675, Oct. 2008.

Vuk-Pavlovic, "Rebuilding immunity in cancer patients," *Blood Cells Mol. Dis.*, 40(1):94-100, print Jan.-Feb. 2008, Epub Sep. 2007.

Xin et al., "Sunitinib inhibition of Stat3 induces renal cell carcinoma tumor cell apoptosis and reduces immunosuppressive cells," *Cancer Res.*, 15;69(6):2506-13, print Mar. 2009, Epub Feb. 2009.

Yang et al., "Low HLA-DR expression on CD14+ monocytes of burn victims with sepsis, and the effect of carbachol in vitro," *Burns*, 34(8):1158-1162, print Dec. 2008, Epub Jun. 2008.

Yu et al., [A study on HLA-Dr expression of brain tumor cells and mononuclear cell subsets infiltrating in these tumors], [Article in Chinese], *Zhonghua Bing Li Xue Za Zhi.*, 23(4):221-223, Aug. 1994 [English abstract only].

International Preliminary Report on Patentability for PCT/US2010/048002, mailed Mar. 22, 2012, 6 pages.

International Search Report and Written Opinion for PCT/US2010/048002, mailed May 2, 2011, 9 pages.

da Silva et al., "Alefacept, an immunomodulatory recombinant LFA-3/IgG1 fusion protein, induces CD16 signaling and CD2/CD16-dependent apoptosis of CD2(+) cells," J Immunol., 168(9):4462-4471, May 1, 2002.

* cited by examiner

DEPLETING IMMUNOSUPPRESSIVE MONOCYTES WITHIN A MAMMAL

CROSS-REFERENCE TO RELATED APPLICATIONS

This application is a National Stage application under 35 U.S.C. 371 and claims benefit under 35 U.S.C. 119(a) of International Application No. PCT/US2010/048002, having an International Filing Date of Sep. 7, 2010, which claims the benefit of U.S. Provisional Application Ser. No. 61/241,227, filed Sep. 10, 2009. The disclosures of the prior applications are considered part of (and are incorporated by reference in) the disclosure of this application.

STATEMENT AS TO FEDERALLY SPONSORED RESEARCH

This invention was made with government support under CA097274 awarded by National Institutes of Health. The government has certain rights in the invention.

BACKGROUND

1. Technical Field

This document relates to methods and materials involved in depleting immunosuppressive monocytes (e.g., $CD14^+/DR^-$ or $CD14^+/DR^{low}$ monocytes) within a mammal. For example, this document relates to methods and materials involved in using a CD2 binding molecule (e.g., alefacept) to deplete immunosuppressive monocytes within a mammal (e.g., a human).

2. Background Information

Monocytes are a type of white blood cell that helps form a mammal's immune system. Monocytes can function to replenish resident macrophages and dendritic cells under normal states, and to move, in response to inflammation signals, quickly to sites of infection in the tissues and differentiate into macrophages and dendritic cells to elicit an immune response. Monocytes are usually identified in stained smears by their large bilobate nucleus.

SUMMARY

This document provides methods and materials related to depleting immunosuppressive monocytes (e.g., $CD14^+/DR^-$ or $CD14^+/DR^{low}$ monocytes) within a mammal. For example, this document relates to methods and materials involved in using a CD2 binding molecule (e.g., alefacept) to deplete immunosuppressive monocytes within a mammal (e.g., a human). The methods and materials provided herein can be used to restore immune function in patients suffering from the presence of immunosuppressive monocytes such as cancer and sepsis patients having detectable levels of immunosuppressive monocytes (e.g., $CD14^+/DR^-$ or $CD14^+/DR^{low}$ monocytes).

In general, one aspect of this document features a method for improving immune function within a mammal. The method comprises, or consists essentially of, (a) identifying a mammal wherein greater than 0.5 percent of the mammal's peripheral blood mononuclear cells are immunosuppressive monocytes, and (b) administering a CD2 binding molecule to the mammal under conditions wherein the number of immunosuppressive monocytes present within the mammal is reduced, thereby improving immune function within the mammal. The mammal can be a human. The identifying step can comprise identifying a mammal wherein greater than 0.75 percent of the mammal's peripheral blood mononuclear cells are immunosuppressive monocytes. The identifying step can comprise identifying a mammal wherein greater than 1 percent of the mammal's peripheral blood mononuclear cells are immunosuppressive monocytes. The identifying step can comprise identifying a mammal wherein greater than 1.25 percent of the mammal's peripheral blood mononuclear cells are immunosuppressive monocytes. The immunosuppressive monocytes can be $CD14^+/HLA-DR^{neg}$ monocytes. The immunosuppressive monocytes can be $CD14^+/HLA-DR^{low}$ monocytes. The CD2 binding molecule can comprise an amino acid sequence from an LFA3 polypeptide fused to an amino acid sequence having the ability to bind to a polypeptide present on the immunosuppressive monocytes. The CD2 binding molecule can be alefacept. The alefacept can be administered in an amount between 0.1 and 0.4 mg/kg of body weight, at a frequency between once a month and twice a week, and for a duration between one week and one year. The number of immunosuppressive monocytes present within the mammal can be reduced by at least 25 percent. The number of immunosuppressive monocytes present within the mammal can be reduced by at least 50 percent. The number of immunosuppressive monocytes present within the mammal can be reduced by at least 75 percent. The number of immunosuppressive monocytes present within the mammal can be reduced by at least 95 percent. The mammal can be a human with cancer. The cancer can be melanoma. The method further can comprise administering a cancer therapy to the mammal. The cancer therapy can be administered to the mammal after the number of immunosuppressive monocytes present within the mammal is reduced. The cancer therapy can be administered to the mammal before the number of immunosuppressive monocytes present within the mammal is reduced. The cancer therapy can be administered to the mammal together with the CD2 binding molecule. The mammal can be a human with sepsis. The method further can comprise administering a sepsis therapy to the mammal. The sepsis therapy can be administered to the mammal after the number of immunosuppressive monocytes present within the mammal is reduced. The sepsis therapy can be administered to the mammal before the number of immunosuppressive monocytes present within the mammal is reduced. The sepsis therapy can be administered to the mammal together with the CD2 binding molecule.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
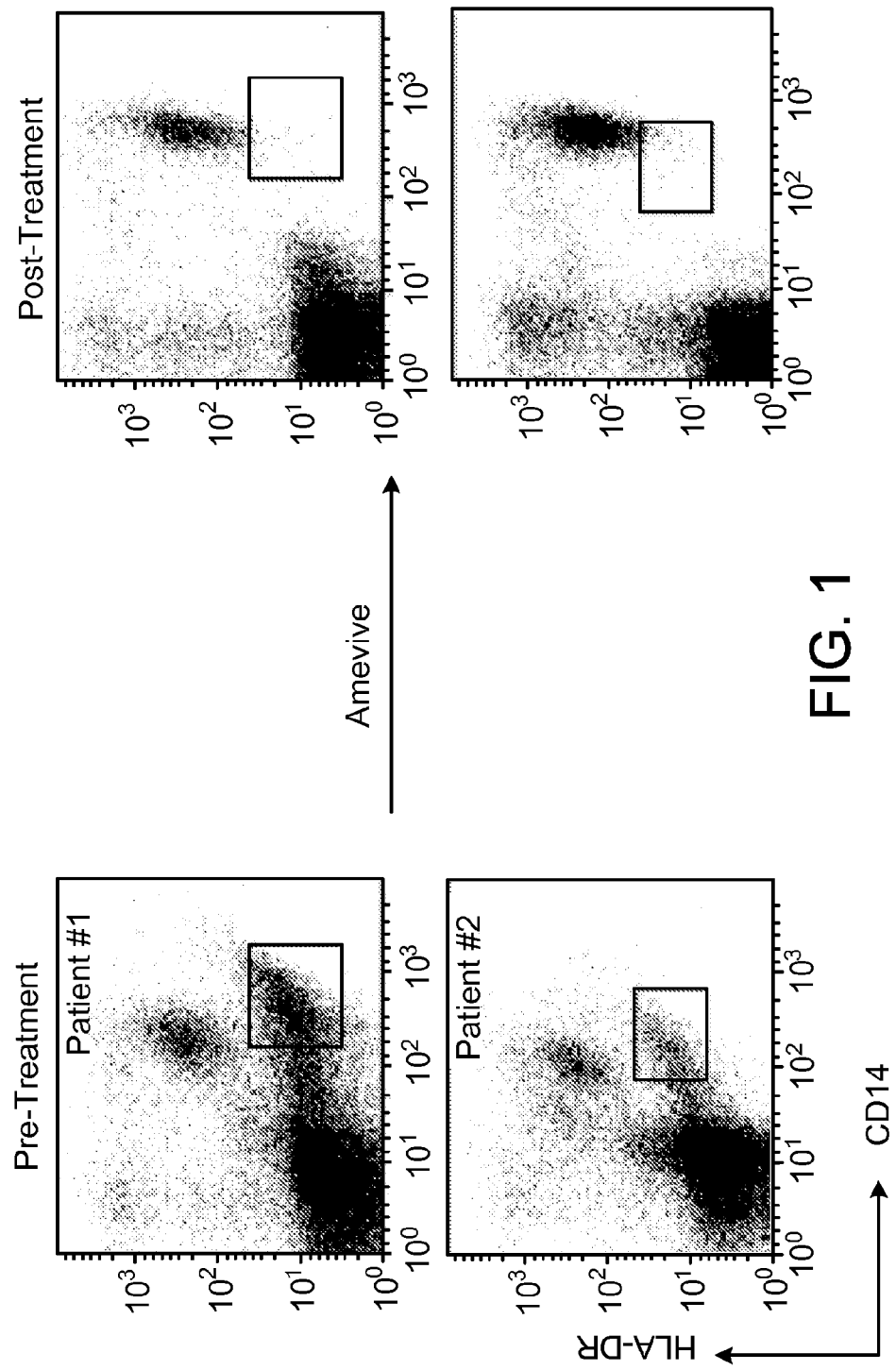
FIG. 1 contains flow cytometry plots of peripheral blood cells from two patients who participated in the phase I/II trial of Amevive® (also known as alefacept) for relapsed T-cell lymphoma. In the left plots, it can be seen that there are two populations of CD14$^+$ monocytes: HLA-DR$^{pos}$ and HLA-DR$^{neg}$. After treatment with Amevive®, both patients had not only an anti-tumor response, but also a disappearance of the CD14$^+$/HLA-DR$^{neg}$ cell population.

This document provides methods and materials related to depleting immunosuppressive monocytes (e.g., CD14$^+$/DR$^-$ or CD14$^+$/DR$^{low}$ monocytes) within a mammal. For example, this document provides methods and materials involved in using a CD2 binding molecule (e.g., alefacept) to deplete immunosuppressive monocytes within a mammal. The term "immunosuppressive monocytes" as used herein refers to monocytes that express CD14 and little or no MHC class II molecules (e.g., little or no HLA-DR molecules). In humans, human CD14$^+$/DR$^-$ monocytes and human CD14$^+$/DR$^{low}$ monocytes are examples of immunosuppressive monocytes.

The methods and materials provided herein can be used to deplete immunosuppressive monocytes in any type of mammal including, without limitation, mice, rats, dogs, cats, horses, cows, pigs, monkeys, and humans. Using the methods and materials provided herein to deplete immunosuppressive monocytes within a mammal can restore normal immune function within the mammal. For example, a human with cancer (e.g., melanoma) or sepsis who has detectable levels of immunosuppressive monocytes can be treated with a CD2 binding molecule (e.g., alefacept) to reduce the number of immunosuppressive monocytes within the human. Reducing the number of immunosuppressive monocytes within a mammal can allow the mammal to mount an effective immune response. For example, a mammal suffering from cancer or sepsis can be treated as described herein to reduce the number of immunosuppressive monocytes such that the mammal's immune system can, in the absence of detectable levels of immunosuppressive monocytes, mount an effective immune response against the cancer cells or infection.

In some cases, a CD2 binding molecule can be used as described herein to reduce the number of immunosuppressive monocytes such that a prior, concurrent, or subsequent treatment approach (e.g., a vaccination approach, a chemotherapy approach, or an antibiotic approach) can be more effective than it would otherwise be in the absence of the depletion of the immunosuppressive monocytes via treatment with the CD2 binding molecule. For example, a cancer patient having detectable levels of immunosuppressive monocytes can be treated with a CD2 binding molecule as described herein to reduce the number of immunosuppressive monocytes. Once the number of immunosuppressive monocytes within the patient is reduced, the patient can be treated with an appropriate chemotherapy. Table 1 provides a list of treatments that can be used in combination with the immunosuppressive monocyte depletion methods provided herein to treat the indicated conditions.

TABLE 1

List of conditions and corresponding treatments that can be combined with the immunosuppressive monocyte depletion methods provided herein.

| Condition | Treatment |
|---|---|
| Sepsis | Antibiotic treatment (e.g., vancomycin, cephalosporins, penicillins, aminoglycosides) |
| Solid Tumors (e.g., melanoma) | Tumor vaccine (e.g., polypeptide or cell-based vaccines); Chemotherapy |
| Hematologic malignancies (e.g., non-Hodgkin Lymphoma) | Tumor vaccine, Chemotherapy, Antibody-based immunotherapy |

Any appropriate method can be used to assess the number of immunosuppressive monocytes present within a mammal. For example, flow cytometry techniques that include the use of anti-CD14 and anti-HLA-DR antibodies can be used as described herein to assess the number of immunosuppressive monocytes present within a human (e.g., present within a blood sample collected from the human).

As described herein, a CD2 binding molecule can be used to reduce the number of immunosuppressive monocytes within a mammal. The term "CD2 binding molecule" as used herein refers to a molecule that exhibits binding affinity (e.g., a $K_d$ less than $1 \times 10^{-4}$, less than $1 \times 10^{-5}$, less than $1 \times 10^{-6}$, less than $1 \times 10^{-7}$, less than $1 \times 10^{-8}$, less than $1 \times 10^{-9}$, or less than $1 \times 10^{-10}$ M) for a CD2 polypeptide. For example, a CD2 binding molecule can have a binding affinity such that the $K_d$ is between 5 μM and 50 μM (e.g., between 9 and 22 μM). In the case of humans, a CD2 polypeptide can have the amino acid sequence set forth in GenBank® gi number 156071472 (accession number NP_001758) and can be encoded by the nucleic acid set forth in GenBank® gi number 156071471 (accession number NM_001767). Examples of CD2 binding molecules include, without limitation, anti-CD2 antibodies (e.g., humanized anti-CD2 antibodies, chimeric anti-CD2 antibodies, single chain anti-CD2 antibodies, monoclonal anti-CD2 antibodies, polyclonal anti-CD2 antibodies, and anti-CD2 antibody fragments), LFA3 polypeptides (e.g., a human LFA3 polypeptide), and LFA3 polypeptide fragments (e.g., a LFA3 fragment that includes the first domain of an LFA3 polypeptide). In the case of humans, a LFA3 polypeptide can have the amino acid sequence set forth in GenBank® gi number 4502677 (accession number NP_001770) and can be encoded by the nucleic acid set forth in GenBank® gi number 221316611 (accession number NM_001779).

In some cases, a CD2 binding molecule can be a fusion polypeptide that includes an anti-CD2 antibody, an LFA3 polypeptide, or an LFA3 polypeptide fragment fused to a polypeptide having the ability to bind (e.g., with a $K_d$ less than $1 \times 10^{-4}$, less than $1 \times 10^{-5}$, less than $1 \times 10^{-6}$, less than $1 \times 10^{-7}$, less than $1 \times 10^{-8}$, less than $1 \times 10^{-9}$, less than $1 \times 10^{-10}$, less than $1 \times 10^{-11}$, or less than $1 \times 10^{-12}$ M) to a polypeptide present on an immunosuppressive monocyte. Examples of polypeptides present on an immunosuppressive monocyte include, without limitation, CD16 polypeptides, CD14 polypeptides, CD11c polypeptides, and CD64 polypeptides. Examples of polypeptides having the ability to bind to a polypeptide present on an immunosuppressive monocyte include, without limitation, the constant region of an immunoglobulin (e.g., an Fc domain) and adhesion polypeptides (e.g., selectins). Table 2 provides a list of polypeptides present on immunosuppressive monocytes together with a corresponding polypeptide having the ability to bind to the listed polypeptide present on immunosuppressive monocytes.

TABLE 2

Polypeptides expressed by immunosuppressive monocytes and their corresponding binding partners.

| Polypeptide expressed by immunosuppressive monocytes | Binding partner |
|---|---|
| CD16 | Fc domain |
| CD64 | Fc domain |
| CD11c | complement |
| B7-H1 (PD-L1) | PD-1 and B7-1 |
| B7-H2 | ICOS |

Figure 2:
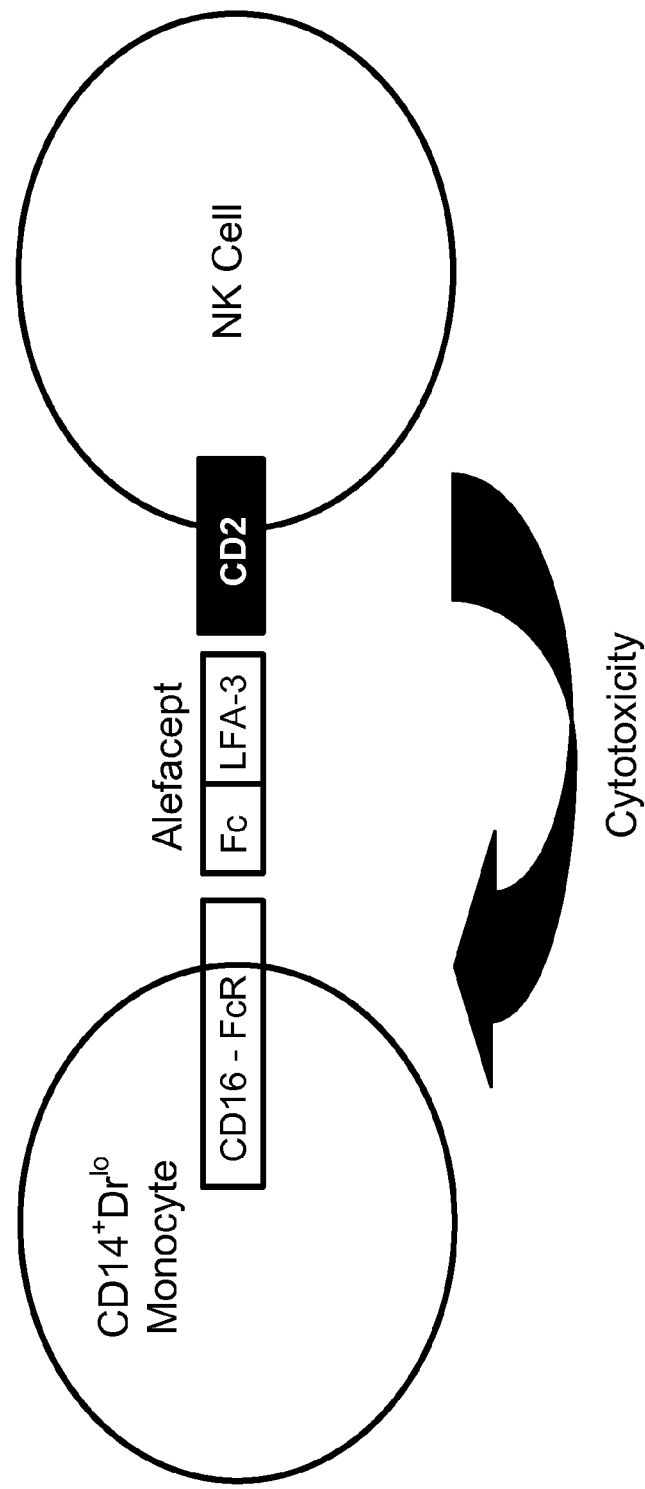
FIG. 2 is a schematic representation of a possible interaction between immunosuppressive monocytes and natural killer cells upon treatment with alefacept.

In one embodiment, a CD2 binding molecule can be a fusion polypeptide having an LFA3 polypeptide fragment fused to an Fc domain. An example of such a CD2 binding molecule is alefacept or LFA-3/IgG1 fusion protein (LFA3TIP), which is described elsewhere (U.S. Pat. No. 6,162,432 and Miller et al., *J. Exp. Med.*, 178(1):211-222 (1993)). As described herein, humans containing immunosuppressive monocytes can be treated with a CD2 binding molecule such as alefacept under conditions that result in a reduction in the number of immunosuppressive monocytes present within the human (FIG. 1). While not being limited to any particular mode of action, a CD2 binding molecule may function to facilitate the interaction of natural killer cells with immunosuppressive monocytes in a manner that results in the depletion of the immunosuppressive monocytes (FIG. 2).

As described herein, a method for reducing the number of immunosuppressive monocytes within a mammal can include administering a CD2 binding molecule to a mammal under conditions that reduce the number of immunosuppressive monocytes within the mammal. In some cases, before administering a CD2 binding molecule (e.g., alefacept), a mammal can be assessed to determine whether or not the mammal contains immunosuppressive monocytes. For example, a method for reducing the number of immunosuppressive monocytes within a human can include (a) identifying a human having a detectable level of immunosuppressive monocytes (e.g., greater than 0.5 percent of peripheral blood mononuclear cells are immunosuppressive monocytes) and (b) administering a CD2 binding molecule to the identified human under conditions that reduce the number of immunosuppressive monocytes within the human. In some cases, a detectable level of immunosuppressive monocytes can be a level such that greater than 0.75 percent (e.g., greater than 1, 1.5, 2, 2.5, 3, 3.5, 4, 4.5, or 5 percent) of peripheral blood mononuclear cells are immunosuppressive monocytes. The level of reduction can be a 25, 30, 35, 40, 45, 50, 55, 60, 65, 70, 75, 80, 85, 90, 95, or more percent reduction. Any appropriate method such as flow cytometry can be used to assess the number of immunosuppressive monocytes present within the mammal.

Any appropriate method can be used to administer a CD2 binding molecule described herein to a mammal. For example, a CD2 binding molecule (e.g., alefacept) can be administered via injection (e.g., subcutaneous injection, intramuscular injection, intratumoral injection, intravenous injection, or intrathecal injection).

An effective amount of a CD2 binding molecule (e.g., alefacept) can be any amount that reduces (e.g., a 25, 30, 35, 40, 45, 50, 55, 60, 65, 70, 75, 80, 85, 90, 95, or more percent reduction) the number of immunosuppressive monocytes present within the mammal without producing significant toxicity to the mammal. Typically, an effective amount of a CD2 binding molecule such as alefacept can be from about 0.05 mg/kg of body weight to about 500 mg/kg of body weight (e.g., about 0.1 mg/kg, about 0.15 mg/kg, about 0.2 mg/kg, about 0.25 mg/kg, about 0.3 mg/kg, about 0.35 mg/kg, or about 0.4 mg/kg). If a particular mammal fails to respond to a particular amount, then the amount can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and the number of immunosuppressive monocytes present may require an increase or decrease in the actual effective amount administered.

The frequency of administration of a CD2 binding molecule (e.g., alefacept) can be any frequency that reduces (e.g., a 25, 30, 35, 40, 45, 50, 55, 60, 65, 70, 75, 80, 85, 90, 95, or more percent reduction) the number of immunosuppressive monocytes present within the mammal without producing significant toxicity to the mammal. For example, the frequency of administration can be from about once a day to about once every other month, or from about once a week to about six times a month, or from about once a month to about three times a year. The frequency of administration can remain constant or can be variable during the duration of treatment. For example, the frequency can be once a week for eight weeks followed by once a month for ten months. A course of treatment with a CD2 binding molecule can include rest periods. For example, a CD2 binding molecule such as alefacept can be administered over a two month period followed by a two month rest period, and such a regimen can be repeated multiple times. As with the effective amount, various factors can influence the actual frequency of administration used for a particular application. For example, the effective amount, duration of treatment, use of multiple treatment agents, route of administration, and the number of immunosuppressive monocytes present may require an increase or decrease in administration frequency.

An effective duration for administering a CD2 binding molecule (e.g., alefacept) can be any duration that reduces (e.g., a 25, 30, 35, 40, 45, 50, 55, 60, 65, 70, 75, 80, 85, 90, 95, or more percent reduction) the number of immunosuppressive monocytes present within the mammal without producing significant toxicity to the mammal. Thus, the effective duration can vary from several days to several weeks, months, or years. In general, the effective duration for the treatment of skin cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and the number of immunosuppressive monocytes present.

This document also provides compositions containing a CD2 binding molecule. Such compositions can be in any appropriate form. For example, a composition containing a CD2 binding molecule can be in the form of a solution or powder with or without a diluent to make an injectable suspension. A composition also can contain additional ingredients including, without limitation, pharmaceutically acceptable vehicles. A pharmaceutically acceptable vehicle can be, for example, saline, water, lactic acid, and mannitol.

After administering a CD2 binding molecule or a composition containing a CD2 binding molecule to a mammal, the mammal can be monitored to determine whether or not the number of immunosuppressive monocytes present within the mammal was reduced. As described herein, flow cytometry can be used to assess the number of immunosuppressive monocytes present within a mammal.

The invention will be further described in the following examples, which do not limit the scope of the invention described in the claims.

EXAMPLES

Example 1

Alefacept Reduces the Number of $CD14^+$/HLA-$DR^{neg}$ Monocytes Within Patients A phase I trial of intravenous Amevive® (alefacept) was initiated to test Amevive® as a single agent in three different cohorts of patients with lymphoma: 0.15 mg of Amevive®/kilogram of body weight IV, 0.20 mg/kilogram IV, and 0.3 mg/kilogram IV. The doses were delivered weekly for eight weeks followed by an evaluation. If the patient responded or was stable, then the patient received one dose IV monthly for ten additional cycles for a total induction of one year. Patients were then observed, and when they progressed, they were reintroduced with eight weekly doses followed by another maintenance. The phase I study was completed with no dose limiting toxicity.

The presence and amounts of $CD14^+$/HLA-$DR^{neg}$ monocytes in patients with lymphoma were investigated. These cells were readily identified by flow cytometry, but they were not detected by a routine complete blood count. Briefly, flow cytometry was performed using fluorochrome-conjugated antibodies against CD14 and HLA-DR. $CD14^+$/HLA-$DR^{neg}$ monocytes exhibited very bright expression of CD16 when compared with an isotype control antibody.

The number of $CD14^+$/HLA-$DR^{neg}$ monocytes did not tend to alter the total monocyte count as determined from the complete blood count. In two patients enrolled in the clinical trial and treated with Amevive®, the $CD14^+$/HLA-$DR^{neg}$ monocytes that were present prior to Amevive® therapy disappeared after Amevive® therapy (FIG. 1). In one of these patients, the $CD14^+$/HLA-$DR^{neg}$ monocytes reappeared at the time of relapse after she had been off the treatment for several months. In the other patient, the $CD14^+$/HLA-$DR^{neg}$ monocytes remained absent, and the patient remained in remission from his cutaneous T-cell lymphoma. Both patients were treated in the 0.2 mg/kg IV cohort. One other patient was evaluated and had a reduction in $CD14^+$/HLA-$DR^{neg}$ monocytes that was significant, but not as striking as these two patients.

Example 2

Clinical Trial to Confirm Use of CD2 Binding Molecules to Reduce the Number of $CD14^+$/HLA-$DR^{neg}$ Monocytes Within Patients About 15 to 20 patients with advanced cancer who have no other reasonable options and have detectable $CD14^+$/HLA-$DR^{neg}$ monocytes in their blood by flow cytometry are enrolled. A multi-color flow cytometry panel is used to quantitate the immunosuppressive monocytes. Briefly, flow cytometry is performed using as described herein or using any combination of the following markers: CD14, CD16 (most are $CD16^-$), HLA-DR, CD115, CX3CR1, CCR2, CD64, and CD32.

Eligibility criteria are advanced, incurable cancer, no other ongoing therapy, the presence of blood $CD14^+$/HLA-$DR^{neg}$ monocytes, and a willingness to visit the clinic weekly for blood tests. Patients are to receive weekly Amevive® at a dose of 0.3 mg/kilogram IV. Patients are seen weekly and receive treatment as long as detectable suppressive monocytes remain in their blood up to eight weekly treatments. Patients are not to receive more than eight weekly treatments. The reason for this limit is that it is the length of time that induced patients in the completed trial with observed effects. If the suppressive monocytes disappear, then the patients are monitored weekly for four weeks followed by every other week for one month followed by monthly for six months to assess the duration of the induced reduction in blood $CD14^+$/HLA-$DR^{neg}$ monocytes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing the number of $CD14^+$/HLA-$DR^{neg}$ or $CD14^+$/HLA-$DR^{low}$ monocytes present in blood of a mammal, wherein said mammal is a human with cancer, wherein said method comprises:
   (a) performing flow cytometry using a blood sample obtained from said mammal to identify said mammal as having a level of $CD14^+$/HLA-$DR^{neg}$ or $CD14^+$/HLA-$DR^{low}$ monocytes wherein greater than 0.5 percent of the mammal's peripheral blood mononuclear cells are $CD14^+$/HLA-$DR^{neg}$ or $CD14^+$/HLA-$DR^{low}$ monocytes,
   (b) administering a CD2 binding molecule to said mammal, wherein the number of $CD14^+$/HLA-$DR^{neg}$ or $CD14^+$/HLA-$DR^{low}$ monocytes present within blood of said mammal is reduced, wherein said CD2 binding molecule comprises an amino acid sequence from an LFA3 polypeptide fused to an amino acid sequence having the ability to bind to a polypeptide present on said $CD14^+$/HLA-$DR^{neg}$ or $CD14^+$/HLA-$DR^{low}$ monocytes.

2. The method of claim 1, wherein greater than 0.75 percent of the mammal's peripheral blood mononuclear cells are $CD14^+$/HLA-$DR^{neg}$ or $CD14^+$/HLA-$DR^{low}$ monocytes.

3. The method of claim 1, wherein greater than 1 percent of the mammal's peripheral blood mononuclear cells are $CD14^+$/HLA-$DR^{neg}$ or $CD14^+$/HLA-$DR^{low}$ monocytes.

4. The method of claim 1, wherein greater than 1.25 percent of the mammal's peripheral blood mononuclear cells are $CD14^+$/HLA-$DR^{neg}$ or $CD14^+$/HLA-$DR^{low}$ monocytes.

5. The method of claim 1, wherein said alefacept is administered in an amount between 0.1 and 0.4 mg/kg of body weight, at a frequency between once a month and twice a week, and for a duration between one week and one year.

6. The method of claim 1, wherein said number of $CD14^+$/HLA-$DR^{neg}$ or $CD14^+$/HLA-$DR^{low}$ monocytes present within said mammal is reduced by at least 25 percent.

7. The method of claim 1, wherein said number of $CD14^+$/HLA-$DR^{neg}$ or $CD14^+$/HLA-$DR^{low}$ monocytes present within said mammal is reduced by at least 50 percent.

8. The method of claim 1, wherein said number of CD14$^+$/HLA-DR$^{neg}$ or CD14$^+$/HLA-DR$^{low}$ monocytes present within said mammal is reduced by at least 75 percent.

9. The method of claim 1, wherein said number of CD14$^+$/HLA-DR$^{neg}$ or CD14$^+$/HLA-DR$^{low}$ monocytes present within said mammal is reduced by at least 95 percent.

10. The method of claim 1, wherein said cancer is melanoma.

11. The method of claim 1, wherein said cancer therapy is administered to said mammal after said number of CD14$^+$/HLA-DR$^{neg}$ or CD14$^+$/HLA-DR$^{low}$ monocytes present within said mammal is reduced.

12. The method of claim 1, wherein said cancer therapy is administered to said mammal before said number of CD14$^+$/HLA-DR$^{neg}$ or CD14$^+$/HLA-DR$^{low}$ monocytes present within said mammal is reduced.

13. The method of claim 1, wherein said cancer therapy is administered to said mammal together with said CD2 binding molecule.

\* \* \* \* \*

UNITED STATES PATENT AND TRADEMARK OFFICE
CERTIFICATE OF CORRECTION

PATENT NO. : 9,289,469 B2
APPLICATION NO. : 13/394787
DATED : March 22, 2016
INVENTOR(S) : Ryan A. Wilcox et al.

Page 1 of 1

It is certified that error appears in the above-identified patent and that said Letters Patent is hereby corrected as shown below:

In the Claims

Column 8, line 44-48 (Claim 1), please delete "wherein said CD2 binding molecule comprises an amino acid sequence from an LFA3 polypeptide fused to an amino acid sequence having the ability to bind to a polypeptide present on said CD14+/HLA-DR$^{neg}$ or CD14$^{+}$/HLA-DR$^{low}$ monocytes."

and insert -- wherein said CD2 binding molecule is alefacept, and (c) administering a cancer therapy to said mammal. --, therefor.

Signed and Sealed this
Thirty-first Day of May, 2016

Michelle K. Lee
*Director of the United States Patent and Trademark Office*